US008900263B2

(12) United States Patent
Fortson

(10) Patent No.: US 8,900,263 B2
(45) Date of Patent: Dec. 2, 2014

(54) SLOTTED INTRODUCER NEEDLE AND METHOD FOR ACCESSING A BODY LUMEN

(75) Inventor: Aaron M. Fortson, Fremont, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 543 days.

(21) Appl. No.: 12/724,278

(22) Filed: Mar. 15, 2010

(65) Prior Publication Data
US 2011/0224713 A1 Sep. 15, 2011

(51) Int. Cl.
*A61B 17/34* (2006.01)
*A61F 11/00* (2006.01)
*A61B 17/08* (2006.01)
*A61B 17/00* (2006.01)
*A61B 17/3205* (2006.01)

(52) U.S. Cl.
CPC ......... *A61B 17/3415* (2013.01); *A61B 17/3417* (2013.01); *A61B 2017/00654* (2013.01); *A61B 2017/00659* (2013.01); *A61B 17/32053* (2013.01)
USPC ............................ 606/185; 606/108; 606/213

(58) Field of Classification Search
USPC ......... 606/166, 167, 153, 133, 184, 185, 222, 606/223; 600/566, 565; 604/272
See application file for complete search history.

(56) References Cited

U.S. PATENT DOCUMENTS

| 3,990,453 | A | * | 11/1976 | Douvas et al. | 606/107 |
| 5,021,059 | A | * | 6/1991 | Kensey et al. | 606/213 |
| 6,921,387 | B2 | * | 7/2005 | Camrud | 604/164.06 |
| 7,670,299 | B2 | * | 3/2010 | Beckman et al. | 600/566 |
| 7,708,721 | B2 | * | 5/2010 | Khaw | 604/264 |
| 2007/0276288 | A1 | * | 11/2007 | Khaw | 600/566 |
| 2009/0209972 | A1 | * | 8/2009 | Loushin et al. | 606/109 |
| 2010/0036400 | A1 | * | 2/2010 | Aboud | 606/153 |

* cited by examiner

*Primary Examiner* — Tuan V Nguyen
(74) *Attorney, Agent, or Firm* — Workman Nydegger; Randy Shen

(57) ABSTRACT

An introducer needle for accessing a body lumen includes an annular-shaped body having a distal end and a proximal end, a leading edge formed on the distal end, and a slot defined in the leading edge and extending proximally from the distal end. In at least one example, the slot can include a first edge and a second edge, the first edge and the second edge each extending proximally from the leading edge and being separated by a central angle greater than 90 degrees and less than 360 degrees. The first end and the second edge are in continuous communication with the leading edge.

19 Claims, 4 Drawing Sheets

SLOTTED INTRODUCER NEEDLE AND METHOD FOR ACCESSING A BODY LUMEN

FIELD OF THE INVENTION

The present invention relates generally to medical devices, and more particular to device, apparatus, and methods for accessing a body lumen.

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath are then removed, leaving a puncture site the size of the needle in the vessel wall. Traditionally, external pressure is then applied to the puncture site until clotting and wound sealing occur. Accordingly, the patient must remain bedridden for a substantial period of time after clotting to ensure closure of the wound. This procedure may be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs.

BRIEF SUMMARY

An introducer needle for accessing a body lumen includes an annular-shaped body having a distal end and a proximal end, a leading edge formed on the distal end, and a slot defined in the leading edge and extending proximally from the distal end.

In at least one example, the slot can be include a first edge and a second edge, the first edge and the second edge each extending proximally from the leading edge and being separated by a central angle greater than 90 degrees and less than 360 degrees. The first end and the second edge are in continuous communication with the leading edge.

A method of accessing a body lumen can include cutting an incision in a body lumen wall in which the incision having a first end and a second end, the first end and the second end being separated by a central angle of less than 360 degrees.

It is to be understood that both the foregoing general description and the following detailed description are exemplary and are intended to provide further explanation of the invention claimed.

BRIEF DESCRIPTION OF THE DRAWINGS

In order to describe the manner in which the above-recited and other advantages and features of the invention can be obtained, a more particular description of the invention briefly described above will be rendered by reference to specific examples thereof that are illustrated in the appended drawings. Understanding that these drawings depict only typical examples of the invention and are not therefore to be considered to be limiting of its scope, the invention will be described and explained with additional specificity and detail through the use of the accompanying drawings.

Figure 1:
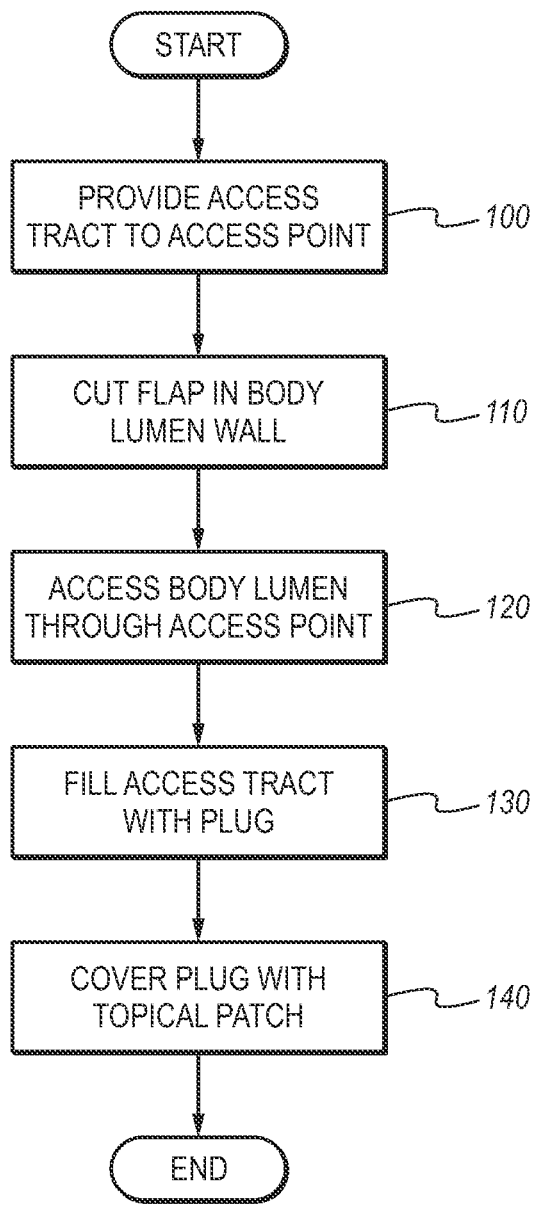
FIG. 1 is a flowchart illustrating a method of accessing a body lumen according to one example.

It should be noted that the figures are not drawn to scale and that elements of similar structures or functions are generally represented by like-reference numerals for illustrative purposes throughout the figures. It also should be noted that the figures are only intended to facilitate the description of examples of the present invention.

DETAILED DESCRIPTION

Devices and methods are disclosed herein for providing access to a body lumen. For example, a tract is cut into the tissue to provide access to the body lumen wall at an access point. At the access point, a flap is cut into the body lumen wall. The flap provides an opening through which medical devices can access the body lumen to perform a medical procedure. Once the medical procedure is complete pressure in the body lumen can return the flap to proximity with the body lumen wall thereby allowing the flap to cover a substantial portion of the opening used to access the body lumen. As a result, the flap reduces the surface area to be sealed to established hemostasis from the body lumen.

The flap can be held in place by a plug of material inserted into the tissue tract. The plug in turn can be held in place as desired by a topical patch. Maintaining the flap to cover a substantial portion of the opening can reduce the surface area of the wound to be healed to the area between the flap and the rest of the body lumen wall. Reducing the surface area of the wound in turn can reduce the healing time associated with accessing the body lumen.

Any device or method can be used to cut the flap in the body lumen. In at least one example, the flap can be cut with a slotted introducer needle that includes an annular-shaped body and a distal tip. A slot can be defined in the distal tip and/or the annular-shaped body that extends proximally of the distal tip. In at least one example, the slot allows the introducer needle to cut the flap in a body lumen wall.

FIG. 1 is a flowchart introducing a method for accessing a body lumen. The method can include providing an access tract to an access point at the body lumen wall, as represented by block 100. In at least one example, assessing the tract can include cutting the tissue to provide the tract. The access point can be at any desired location to access any desired body lumen through any body lumen wall.

Following providing the access tract, the method can include cutting a flap in the body lumen wall, as represented by block 110. Cutting a flap can include making an incision in the body lumen wall that has an open shape. The resulting flap can include a base end that remains connected to the body lumen wall and a tag end that is free from the rest of the body lumen wall. In such a process, a base portion of the flap will remain attached to the body lumen wall while the rest of the flap will be able to move relative to the body lumen wall. Cutting a flap can provide an access opening of a suitable size while reducing the surface area of the wound after the procedure to the perimeter of the flap rather than the entire area of the opening as will be discussed in more detail below.

The flap can be cut by any method or process using any device or devices. In at least one example, a slotted introducer needle similar to those described below can be used to cut the flap in the body lumen wall. Further, the flap can be cut in one or more steps using one or more devices. For ease of reference, a process will be described in which the flap is cut in a single step by a single device.

Continuing with the method of FIG. 1, once the flap has been cut in the body lumen wall, the body lumen can be accessed at the body lumen as represented by block 120. In particular, medical devices can be inserted into the body lumen by way of the opening formed by the flap to perform a medical procedure. Any number of medical devices can access the body lumen wall to perform any number and types of medical procedures.

Once the medical procedure(s) is complete, the devices are removed from the body lumen, and a plug can be inserted into the tissue tract, as represented by block 130. In at least one example, the plug can be formed of a bioabsorbable material. The plug can help establish hemostasis by blocking the flow of blood or other fluid that may flow through the incision between the flap and the rest of the body lumen wall. In particular, the surface area through which the body fluid can flow out of the body lumen wall can be reduced to the space between the incision and the flap as the flap is returned to a position adjacent the body lumen wall.

An optional topical patch can also be applied over the plug, as represented by block 140. The topical patch can help maintain the plug in communication with the flap as well as containing any bodily fluid that may seep through the plug. Accordingly, a process for accessing a body lumen has been introduced in which a flap is cut into a body lumen wall to provide access to a body lumen. Cutting a flap can simultaneously provide an effective opening of sufficient size to provide the desired access while reducing the surface area of the wound that is left to seal to the perimeter of the incision used to cut the flap. Reducing the surface area left to be sealed can allow the wound to seal more quickly.

Figure 2A:
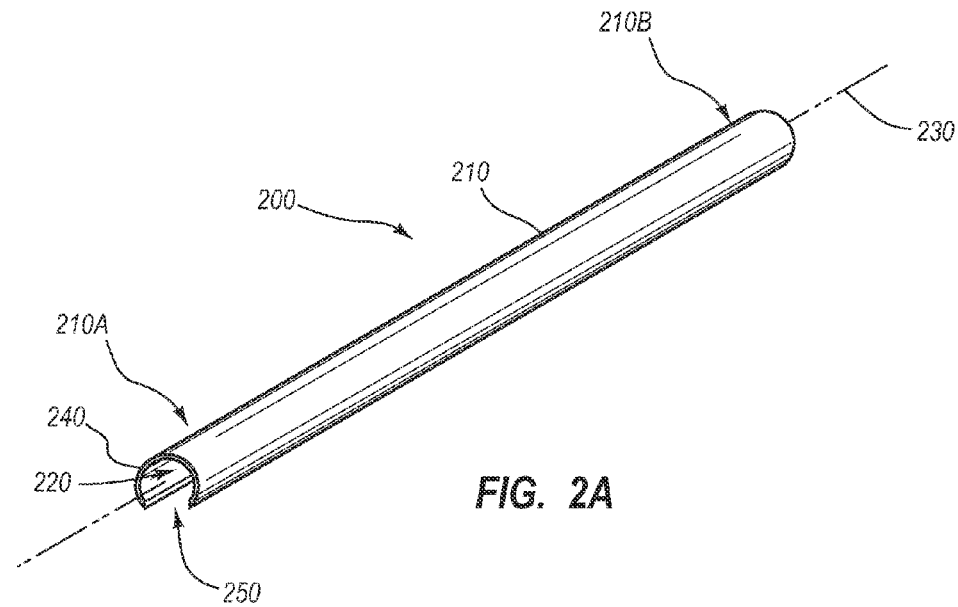
FIG. 2A is a perspective view of a slotted introducer needle according to one example.
Figure 3A:
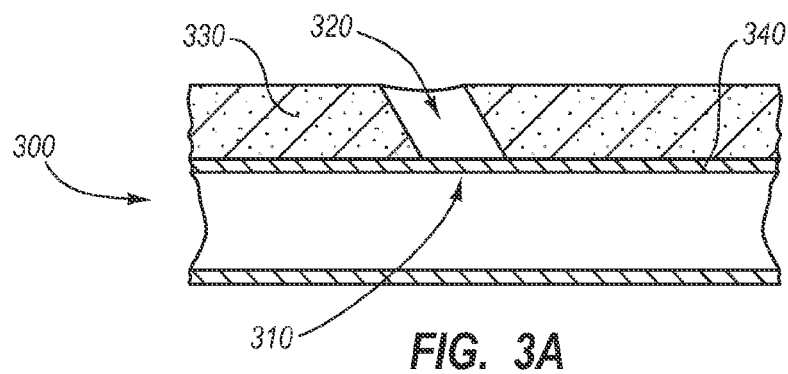
FIGS. 3A-3E illustrate a method of accessing a body lumen with a slotted introducer needle according to one example.

FIG. 2A illustrates a perspective view of a slotted introducer needle 200 configured to cut a flap in a body lumen wall. The slotted introducer needle 200 can include an annular-shaped body 210 having a distal end 210A and a proximal end 210B. A central lumen 220 extends through the annular-shaped body 210 that includes a central axis 230. The slotted introducer needle 200 also includes a leading edge 240 on the distal end 210A of the annular-shaped body 210. A slot 250 is formed in the distal end 210A of the annular-shaped body 210. The slot 250 provides a gap in the leading edge 240 as it is brought into contact with a body lumen wall. The gap in the leading edge 240 in contact with a body lumen wall in turn can allow the slotted introducer needle 200 to cut a flap in the body lumen wall 340 (FIG. 3A).

Figure 2B:
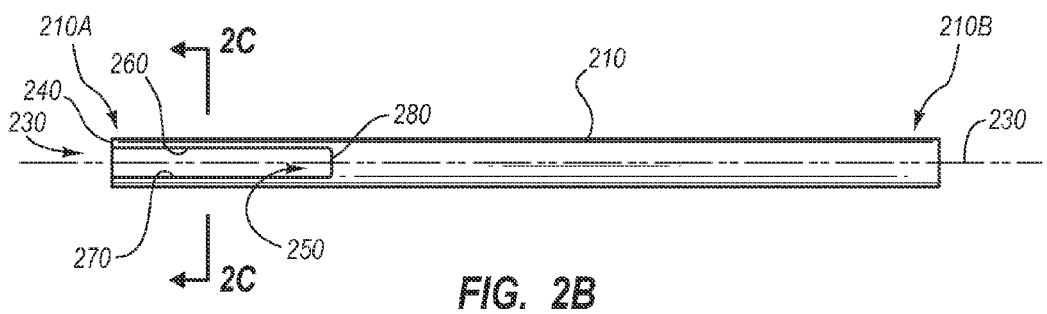
FIG. 2B illustrates a plan view of a slotted introducer needle according to one example.

As shown in FIG. 2B, the slot 250 can defined by the space between edges 260, 270 that extend proximally from the distal tip 210A. In at least one example, the edges 260, 270 can be generally parallel. Further, the edges 260, 270 can be generally parallel to the central axis 230. In the illustrated example, the slot 250 can end distal of the proximal end 210B, such as at a slot terminus 280. The slot terminus 280 connects the edges 260, 270. As a result, at least a portion of the annular-shaped body 210, including the distal end 210A and a portion of the distal end 210A proximal the distal end 210A, have an open and/or discontinuous cross-section.

Figure 2D:
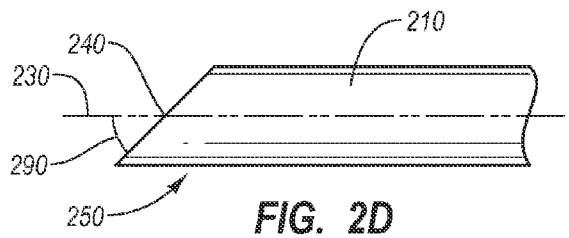
FIGS. 2D-2E illustrate an angle between the central axis and the leading edge.
Figure 2E:
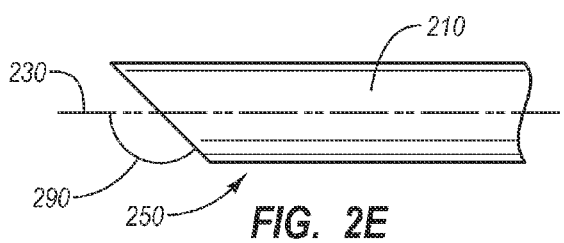
Figure 2C:
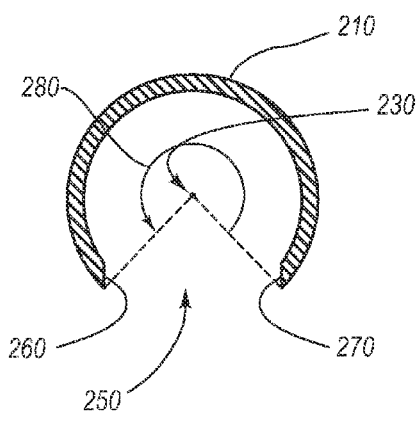
FIG. 2C illustrates a cross-sectional view of the slotted introducer needle of FIG. 2B taken along section 2C-2C.

FIG. 2C illustrates a cross sectional view of the annular-shaped body 210 adjacent the distal end 210A (FIGS. 2A, 2B) that has an open and/or discontinuous cross section. In such an example, the annular-shaped body 210 has a central angle 280 that is greater than 90 degrees but less than 360 as taken internally between the edges 260, 270. For example, the central angle 280 can be greater than 180 degrees and less than 360 degrees, such as less than about 270 degrees. In the illustrated example, the annular-shaped body 210 has a generally arc-shaped cross section.

It will be appreciated that the annular-shaped body 210 and the distal end 210A in particular can have any cross-sectional shape in which a slot 250 is defined in the leading edge and extends proximally from the leading edge into the annular-shaped body. For example, the distal end can have a rounded rectangular section having a generally U-shaped profile, C-shaped profile or any other section with rounded corners. The distal end 210A can also have any combination of curved and/or straight sections to define a slot, including profiles having sharp corners. Thus, although an annular-shaped body may be circular, it may include other noncircular shapes as well, such as elliptical or other shapes that are asymmetrical about a central axis. In other examples, the annular-shaped body 210 may include other shapes and/or may not have a central axis.

It will also be appreciated that while a parallel-edged slot is described that is also generally parallel to the central axis of the lumen defined by the annular-shaped body, other configurations are possible in which one or more of the edges are curved and/or otherwise non-linear and/or in which the edges that define the slot are oriented at some angle relative to the central axis.

Further, in the illustrated example the leading edge 240 is generally perpendicular to the central axis 230 and is also generally planar. It will be appreciated that the leading edge 240 can have any shape, including any combination of curved and/or straight portions that can also be oriented at any angle relative to the central axis 230, as illustrated in FIGS. 2D-2E.

In particular, FIG. 2D illustrates an angle 290 between the central axis 230 and the leading edge 240. The angle 290 shown is such that the leading edge 240 angles proximally away from the slot 250 formed in the annular-shaped body 210. FIG. 2E illustrates the leading edge 240 oriented so as to form an angle 290' between the central axis 230 and the ledge edge 240. In the example illustrated in FIG. 2E, the leading edge 240 angles distally away from the slot 250 formed in the annular shaped body 210. Accordingly, the distal end 210A can have any combination of shapes and orientations in which a slot is defined in the leading edge 240 and extends proximally away from the leading edge 240. Such a configuration can allow the slotted introducer device to cut a slot in a body lumen wall as part of a medical procedure.

FIGS. 3A-3E illustrate a method of accessing a body lumen according to one example. As illustrated in FIG. 3A, a body lumen 300 can be accessed at a desired access point 310 by cutting a tissue tract 320 in tissue 330 adjacent a body lumen wall 340 of the body lumen 300. This can be achieved by the slotted introducer needle 200 or any other device or apparatus can be used to cut the tissue tract 320 as desired, such as a cutting cannula or other cutting device.

Figure 3B:
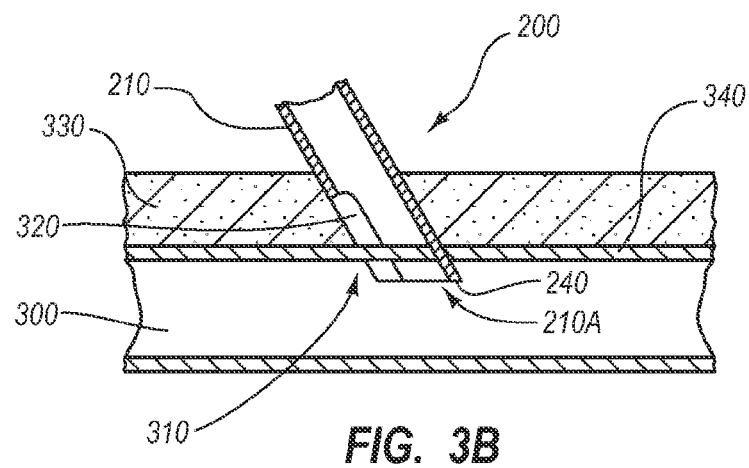

As shown in FIG. 3B, the slotted introducer needle 200 can be advanced through the tissue tract 320 (FIG. 3A) until the leading edge 240 of the distal end 210A is in contact with the body lumen wall 340. The slotted introducer needle 200 can then be advanced distally to cause the lead edge 240 to cut an incision through the body lumen wall 340, and pass at least painfully into the body lumen at the access point 310.

Figure 3C:
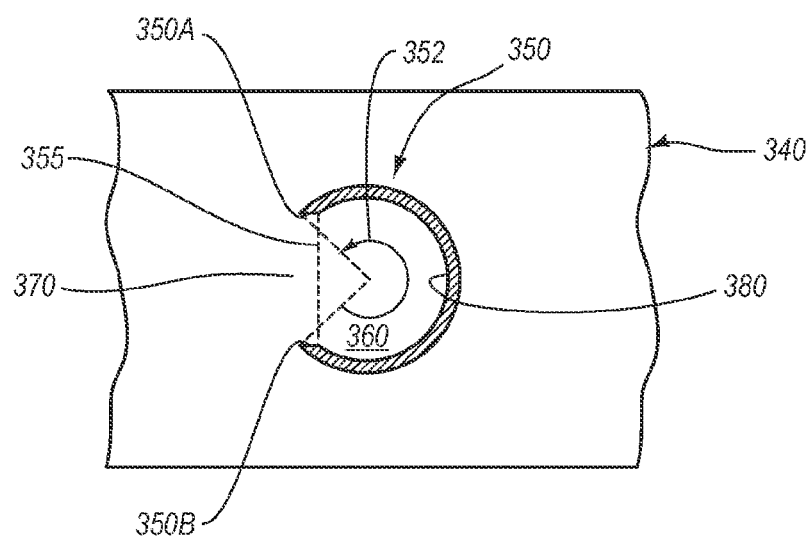

An incision 350 in the body lumen wall 340 is shown in FIG. 3C. As shown in FIG. 3C, the incision 350 includes ends 350A, 350B that are separated by a central angle 352 that is less than 360 degrees. Accordingly, the incision 350 defines a flap 360. The flap 360 can include a base portion 370 and a tag end 380. The base portion 370 remains attached to the rest of the body lumen wall 340. In such an example, the flap 360 can be moved to provide an opening having a size approximately equal to the area circumscribed by the incision 350 and a chord 355 across the base portion 370 of the flap 360.

Figure 3D:
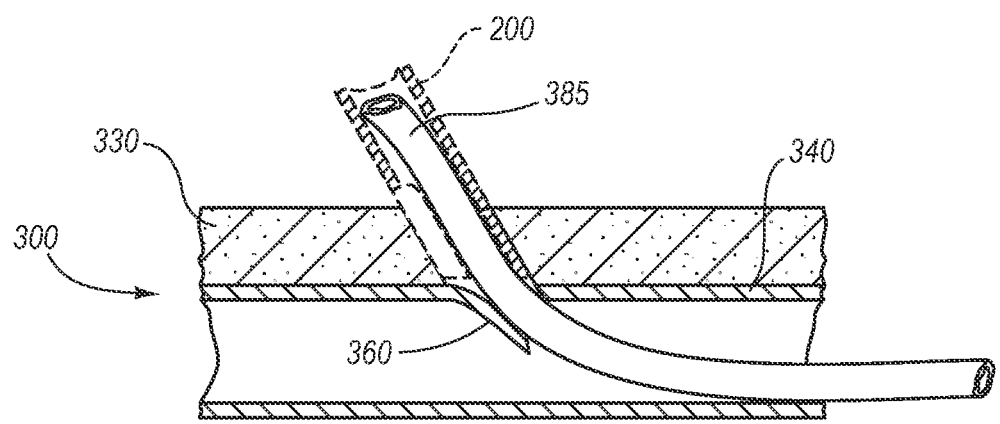

As illustrated in FIG. 3D, once the flap 360 has been formed or cut, the flap 360 can be urged into the body lumen 300 to expand the incision to provide access through the body lumen wall 340. For example, an instrument 385, such as a medical device, can then be introduced to the body lumen 300 as shown in FIG. 3D. In the illustrated example, the instrument 385 is passed through the slotted introducer needle 200. It will be appreciated that the instrument 385 can be passed through the flap 360 in any manner to perform a medical procedure or procedures. Once the medical procedure is complete, the instrument 385 can be removed.

Figure 3E:
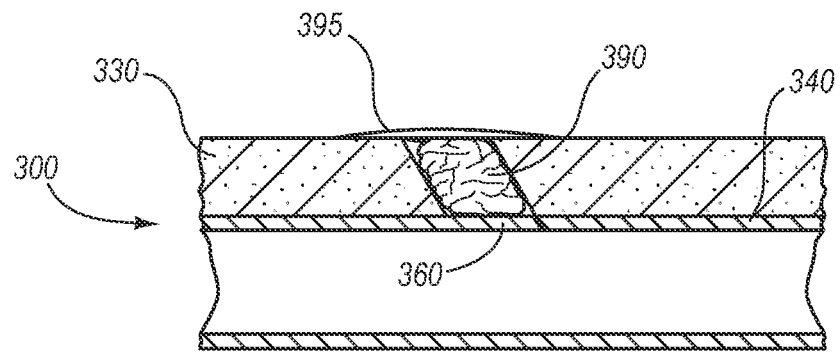

In at least one example, a flow of fluid through the body lumen 300 and/or pressure associated with the flow of fluid can urge the flap 360 toward the rest of the lumen wall 340, as shown in FIG. 3E after the instrument 385 (FIG. 3D) and the slotted introducer needle 200 are removed. Stated another way, the flap 360 is orientated substantially in a direction of the flow of the fluid within the body lumen 300 such that the base portion 370 is located upstream of the free portion, such as the tag end 380. A plug 390 can be inserted into the tissue tract 320 (FIG. 3A) to provide hemostasis. In at least one example, the plug 390 can be formed of a bioabsorbable material. Biodegradable or bioabsorbable, as defined herein, means the composition will degrade or erode in vivo to form smaller chemical species. Degradation can result, for example, by enzymatic, chemical, and physical processes. Suitable biocompatible, biodegradable polymers include, for example, poly(lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, blends and copolymers thereof.

An optional topical patch 395 can then be placed over the plug 390 as desired. Any conventional and/or self-adhesive pad may be applied. Additional benefit can be achieved through the application of a pad chemically treated or including substances that attract the negatively charged red place cells and platelets, effects vasoconstriction, and/or forms a strong clot. Such substances can include, without limitation, Chitosan and thrombin. In such an example, the surface area of the body lumen wall 340 left to be sealed can be reduced as the tag end 380 can return to proximity with the rest of the body lumen wall 340. Accordingly, the surface area to be sealed can correspond to a gap between the body lumen wall 340 and the flap 360, which can be approximately equal to the surface area of the incision 350 (FIG. 3C) rather than the effective size of the opening described above. A relative smaller area to be sealed can allow the access point 310 (FIG. 3A) to seal in a relatively short time.

The invention is susceptible to various modifications and alternative means, and specific examples thereof have been shown by way of example in the drawings and are herein described in detail. It should be understood, however, that the invention is not to be limited to the particular devices or methods disclosed, but to the contrary; the invention is to cover all modifications, equivalents, and alternatives falling within the spirit and scope of the claims.

What is claimed is:

1. A method of accessing a body lumen, comprising:
    positioning an introducer needle adjacent to a body lumen wall, the introducer needle having an annular-shaped body with a distal end and a proximal end, the distal end having an open perimeter leading edge with a slot defined therein, the slot extending proximally from the leading edge;
    cutting an incision in the body lumen wall to form a flap in the body lumen wall, the flap having a base portion attached to the body lumen wall and a free portion extending from the base portion, a perimeter of the free portion approximating the open perimeter leading edge of the introducer needle, the incision having a first end and a second end each terminating at the base portion, the first end and the second end being separated by a central angle of less than 360 degrees to form the base portion of the flap in the body lumen wall, the flap being oriented substantially in a direction of the flow of fluid within the body lumen such that the base portion is located upstream of the free portion;
    accessing the incision with one or more medical devices; and
    disposing a plug adjacent to the incision following removal of the one or more medical devices.

2. The method of claim 1, wherein the central angle is less than 270 degrees.

3. The method of claim 1, wherein the central angle is greater than 90 degrees.

4. The method of claim 1, wherein the central angle is greater than 180 degrees.

5. The method of claim 1, wherein cutting the incision includes cutting an arc-shaped incision.

6. The method of claim 1, wherein cutting the incision includes cutting a u-shaped incision.

7. A method of accessing a body lumen, comprising:
    positioning an introducer needle adjacent to a body lumen wall, the introducer needle having an annular-shaped body with a distal end and a proximal end, the distal end having an open perimeter leading edge with a slot defined therein, the slot extending proximally from the leading edge;
    cutting an incision in the body lumen wall to form a flap in the body lumen wall, the flap having a base portion attached to the body lumen wall and a free portion extending from the base portion, a perimeter of the free portion approximating the open perimeter leading edge of the introducer needle, the incision having a first end and a second end each terminating at the base portion, the first end and the second end being separated by a central angle of greater than 90 degrees and less than 360 degrees to form the base portion of the flap in the body lumen wall, the flap being oriented substantially in a direction of the flow of fluid within the body lumen such that the base portion is located upstream of the free portion;
    accessing the incision with one or more medical devices; and
    disposing a plug adjacent to the incision following removal of the one or more medical devices.

8. The method of claim 7, further comprising advancing the introducer needle through a tissue tract to the body lumen wall.

9. The method of claim 7, wherein accessing the incision with the one or more medical devices includes advancing the one or more medical devices through the incision to move the flap.

10. The method of claim 7, wherein cutting the incision includes cutting an arc-shaped incision, a U-shaped incision, or a C-shaped incision.

11. A method of accessing a body lumen, comprising:
advancing an introducer needle through a tissue tract toward a body lumen wall, the introducer needle having an annular-shaped body with a distal end and a proximal end, the distal end having an open perimeter leading edge with a slot defined therein, the slot extending proximally from the open perimeter leading edge;
making an opening in the body lumen by cutting an incision in the body lumen wall to form a flap in the body lumen wall, the flap having a base portion attached to the body lumen wall and a free portion extending from the base portion, the base portion having a configuration approximating the slot and a perimeter of the free portion approximating the open perimeter leading edge of the introducer needle, the incision having a first end and a second end each terminating at the base portion, the first end and the second end being separated by a central angle of greater than 90 degrees and less than 360 degrees to form the base portion of the flap in the body lumen wall, the flap being oriented substantially in a direction of the flow of fluid within the body lumen such that the base portion is located upstream of the free portion;
moving the free portion from an original position and away from the body lumen wall to allow access with a medical device into the body lumen through the opening; and
at least partially covering the opening by returning the flap toward the original position to facilitate hemostasis.

12. The method of claim 11, wherein cutting the incision in the body lumen wall comprises cutting the incision in the body lumen with the open perimeter leading edge having an arc shape, a U-shape, or C-shape.

13. The method of claim 11, wherein cutting the incision in the body lumen wall comprises cutting the incision in the body lumen with the open perimeter leading edge being perpendicular relative to a central axis of the annular-shaped body.

14. The method of claim 11, wherein cutting the incision in the body lumen wall comprises cutting the incision in the body lumen with the open perimeter leading edge being oriented at an angle relative to the central axis of the annular-shaped body.

15. The method of claim 11, wherein cutting the incision in the body lumen wall comprises cutting the incision in the body lumen with the introducer needle having a first edge and a second edge being generally parallel to one another.

16. The method of claim 15, wherein the first edge and the second edge are generally parallel to a central axis of the annular-shaped body.

17. The method of claim 11, further comprising disposing a plug adjacent to the incision following removal of the one or more medical devices.

18. The method of claim 17, further comprising placing a topical patch over the plug.

19. The method of claim 11, wherein moving the free portion from the original position and away from the body lumen wall comprises moving the free portion into interior of the body lumen.

* * * * *